United States Patent [19]

Markbreiter et al.

[11] 4,252,548

[45] Feb. 24, 1981

[54] CARBON DIOXIDE REMOVAL FROM METHANE-CONTAINING GASES

[75] Inventors: Stephen J. Markbreiter, Edison, N.J.; Irving Weiss, Brooklyn, N.Y.

[73] Assignee: Kryos Energy Inc., New York, N.Y.

[21] Appl. No.: 196

[22] Filed: Jan. 2, 1979

[51] Int. Cl.² .............................................. F25J 1/02
[52] U.S. Cl. .................................... 62/17; 62/23; 62/41; 55/68; 55/89
[58] Field of Search ............... 55/68, 89; 62/17, 23

[56] References Cited

U.S. PATENT DOCUMENTS

| | | | |
|---|---|---|---|
| 3,130,026 | 4/1964 | Becker | 62/17 |
| 3,453,835 | 7/1969 | Hochgesand | 62/17 |
| 3,640,052 | 2/1972 | Konoki et al. | 55/68 |
| 3,977,203 | 8/1976 | Hinton et al. | 62/17 |

Primary Examiner—Norman Yudkoff
Attorney, Agent, or Firm—Paul W. Garbo

[57] ABSTRACT

Methane-containing gases with an appreciable content of carbon dioxide are scrubbed with cold methanol to remove the bulk of the carbon dioxide in a simple system comprising a single gas-liquid contact column and featuring regeneration of the methanol containing carbon dioxide solely by multiple-stage flashing. Land-fill gases containing methane and carbon dioxide as the principal components can be economically processed in such a system to yield methane-rich fuel gases.

9 Claims, 1 Drawing Figure

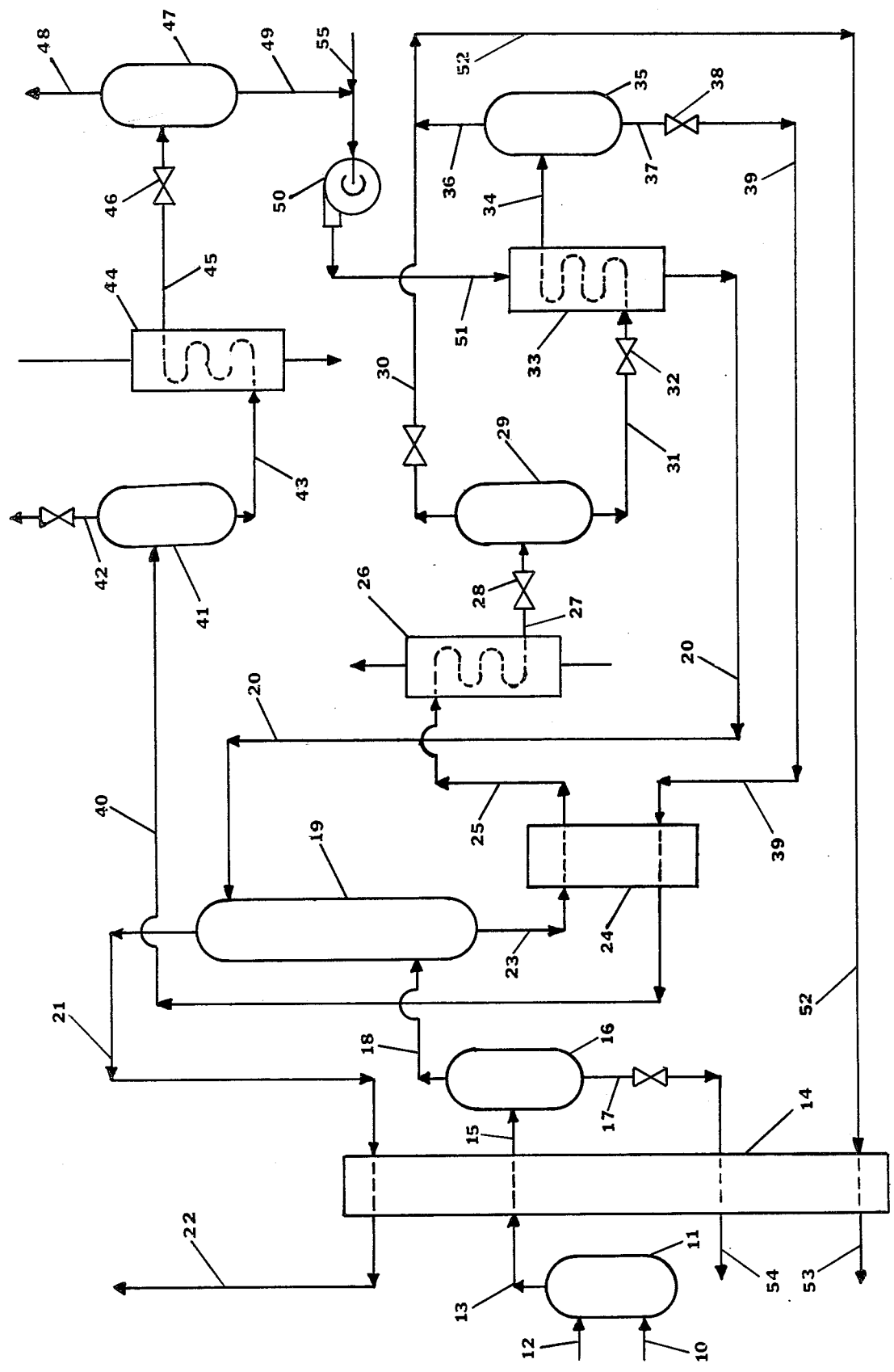

CARBON DIOXIDE REMOVAL FROM METHANE-CONTAINING GASES

BACKGROUND OF THE INVENTION

Many cities have for a long time disposed of garbage by burying it in surrounding areas which are often of low grade level. Hence, such garbage disposal also serves as land fill. The buried garbage decomposes and generates gas containing methane and carbon dioxide as the principal components. Such garbage gas, euphemistically called land-fill gas, has attracted attention as a potential fuel gas in view of its methane content, generally in the range of about 50 to 70% by volume. Carbon dioxide being the other principal component of land-fill gas, generally in the range of about 25 to 45% by volume, must be materially eliminated before the land-fill gas can be utilized in existing fuel gas distribution systems.

The removal of carbon dioxide from gas mixtures is an extensive art. Known processes for the separation of carbon dioxide from other gases utilize refrigeration to cause solid carbon dioxide deposition, a molecular sieve to capture carbon dioxide, chemical absorption, or a system combining such techniques. Scrubbing a gas with methanol to remove carbon dioxide has been incorporated in several different processes which require considerable equipment and, hence, a high capital expenditure.

Methane-containing gases with a high content of carbon dioxide, such as land-fill gases, have not heretofore been seriously considered for fuel purposes because of the high cost of separating carbon dioxide therefrom by known methods.

Accordingly, a principal object of this invention is to provide a process for economically removing a major portion of the carbon dioxide present in gases in which methane is the principal component.

Another object is to provide a simplified plant for eliminating the bulk of the carbon dioxide in gases having a predominant content of methane.

A further object is to treat methane-containing gases having an appreciable content of carbon dioxide to yield fuel gases of high heating value.

These and other objects and advantages of the invention will be evident from the description which follows:

SUMMARY OF THE INVENTION

In accordance with this invention, a gas mixture having methane as the predominant component and an appreciable content of carbon dioxide is scrubbed with cold methanol to separate therefrom a major portion of the carbon dioxide content and thus yield a methane-enriched gas of high heating value. A feature of the invention is the use of a simplified plant having a single gas-liquid contact column for scrubbing the gas mixture with cold methanol and multiple-stage flashing equipment to release carbon dioxide from the methanol leaving the contact column and thus regenerate the methanol so that it can be recycled to the contact column.

While the invention is directed preferably to land-fill gases, herein broadly defined as gas mixtures containing about 50 to 70% by volume of methane and about 25 to about 45% by volume of carbon dioxide, the invention is more generally applicable to gas mixtures containing as the principal component at least about 50% by volume of methane and at least about 5% by volume of carbon dioxide to obtain methane-enriched gases containing not more than approximately 2.5% by volume of carbon dioxide.

Inasmuch as pipelines for fuel gases are usually maintained at pressures of at least about 200 pounds per square inch absolute (psia), a land-fill gas or similar gas mixture containing at least about 50% by volume of methane and at least about 5% by volume of carbon dioxide is compressed to a pressure higher than the pressure of the pipeline into which the methane product gas is injected so as to compensate for the pressure drop of the gas flowing through the system. To attain the desired high pressure, the land-fill gas is compressed in several stages with intermediate cooling of the gas and removal of condensed moisture. Such conventional multiple-stage compression of the gas delivers the gas in partially dehydrated form at the desired pressure and a temperature of approximately 100° F. However, the gas is still saturated with moisture at the delivery pressure and temperature, and will require treatment to eliminate the residual moisture in the gas prior to its entry into the methanol scrubbing column.

The removal of the residual moisture in the land-fill or similar gas is partially achieved by conventional cooling of the gas to a temperature of about 40° F. and separating condensed moisture. Then, the completion of the dehydration of the gas is attained by injecting a small quantity of methanol into the cooled gas and further chilling the gas to a temperature below 0° F. to condense substantially all the residual moisture and the bulk of the methanol in the gas. The thus treated gas, substantially free of moisture and methanol, is discharged into the base portion of the methanol scrubbing column.

The pressure in the scrubbing column is about 10 psi above the pressure of the pipeline, generally at least about 200 psia, into which the scrubbed gas is to be introduced. Higher pressures in the contact or scrubbing column are favorable to the removal of carbon dioxide from the scrubbed gas. However, to minimize the cost of compression, the gas is usually introduced into the scrubbing column at a pressure only about 10 psi above the pressure of the pipeline which will receive the scrubbed gas. Obviously, where a given land-fill gas is to be scrubbed prior to introduction into a pipeline maintained at a pressure of 500 psia, the carbon dioxide content of the scrubbed gas will be lower than that of the same land-fill gas which has been scrubbed at a lower pressure for introduction into a pipeline maintained at a pressure of 300 psia. Accordingly, one variable which can be used to control or limit the residual carbon dioxide content of the scrubbed gas is the pressure in the scrubbing column; increasing that pressure lowers the residual carbon dioxide content of the scrubbed gas.

Two other variables that can be used to limit the residual carbon dioxide content of the scrubbed gas are the temperature of the methanol entering the top of the scrubbing column and the residual carbon dioxide content of the methanol recycled to the column; the lower that temperature is, the lower will be the residual carbon dioxide content of the scrubbed gas. Similarly, the lower the residual carbon dioxide content of the methanol recycled to the column is, the lower will be the residual carbon dioxide content of the scrubbed gas.

Clearly, the reduction of the temperature of the recycled methanol involves the cost of refrigeration while the reduction of the residual carbon dioxide content of the recycled methanol involves the cost of heat applied to the methanol before the last stage of flashing and, more importantly, the cost of consequent increased loss of methanol during the flashing of carbon dioxide. Hence, the treatment of each land-fill or similar gas pursuant to this invention should preferably be conducted under such conditions that the costs of compressing the gas, of refrigerating the recycled methanol, and of reducing the residual carbon dioxide content of the recycled methanol entering the contact tower are substantially optimized, i.e., are adjusted or controlled so that the total cost is minimized.

For most cases that will be encountered, the three control variables are set so that the contact tower will be at a pressure in the range of about 200 to 600 psia, the recycled methanol will enter the column at a temperature in the range of about −40° to −70° F. and the residual carbon dioxide content of the recycled methanol entering the column will be in the range of about 1 to 2% on a molar basis.

As previously mentioned, a small quantity of methanol is injected into the gas before it is chilled to temperatures below the freezing point of water in order to prevent the deposition of ice on the surfaces of the chilling heat exchanger and yet achieve dehydration of that gas by condensing the moisture in the gas in the form of a liquid mixture of water and methanol which is easily separated from the gas. The small quantity of injected methanol is determined principally by the quantity required to prevent ice deposition in the chilling heat exchanger but also by the quantity incidentally lost with the carbon dioxide which is stripped from the methanol recycled to the scrubbing column. In short, the quantity of injected methanol should equal the total quantity of methanol discharged from the system as a liquid mixture of water and methanol and as a vapor mixture of carbon dioxide and methanol. For most cases, an adequate injection of methanol will fall in the range of about 10 to 25 pounds of methanol for each pound of residual moisture in the compressed, cooled land-fill gas to be chilled prior to introduction into the scrubbing column.

BRIEF DESCRIPTION OF THE DRAWINGS

The further description of the invention will refer to the appended drawing which is the diagram of a preferred system of the invention for removing carbon dioxide from a land-fill gas.

DESCRIPTION OF PREFERRED EMBODIMENT

Compressed, cooled land-fill gas in line 10 enters mixing vessel 11 where it is admixed with a small quantity of methanol supplied by line 12. The gaseous mixture flows through line 13 to heat exchanger 14 wherein the mixture is sufficiently chilled so that substantially all of the moisture in the land-fill gas and the bulk of the methanol supplied by line 12 are condensed as a liquid mixture. The chilled stream leaving heat exchanger 14 through line 15 discharges into separator 16. The liquid mixture of water and methanol drops out and leaves separator 16 through line 17 while the dehydrated gas passes through line 18 into the base portion of contact column 19. Cold menthanol from line 20 enters the top portion of column 19 and flows downwardly through trays or packing in column 19 to effect countercurrent scrubbing of the rising gas stream. The scrubbed gas leaves the top of column 19 through line 21 and flows through heat exchanger 14 to transfer its refrigeration to the land-fill gas entering exchanger 14 from line 13. The thus warmed scrubbed gas passes from heat exchanger 14 through line 22 as product gas to a desired utilization point.

The methanol with absorbed carbon dioxide reaching the bottom of column 19 flows through line 23, cooling heat exchanger 24, line 25, refrigerated exchanger 26 and line 27. The pressure of the liquid stream in line 27 is sharply decreased by passage of the stream through reducing valve 28 to effect the first stage of flashing of carbon dioxide from the liquid stream. The discharge from valve 28 enters separator 29 where the vaporized carbon dioxide rises and exits through line 30 while the liquid stream dropping to the bottom of separator 29 passes through line 31, flow-control valve 32 and heat exchanger 33 to give up some of its refrigeration before discharging via line 34 into separator 35. Heating the liquid stream from line 31 in exchanger 33 effects the second stage of flashing carbon dioxide therefrom. Again, vaporized carbon dioxide rises and exits from separator 35 through line 36 while liquid drains from separator 35 through line 37 having flow-control valve 38.

The stream flowing through valve 38 and line 39 passes through heat exchanger 24 to transfer refrigeration to the methanol containing absorbed carbon dioxide drawn from column 19 by line 23. Thence, the heated stream passes through line 40 to separator 41 to complete the third carbon dioxide flashing stage. Vaporized carbon dioxide is vented from separator 41 through valved line 42 while liquid drains through line 43 for passage through warming heat exchanger 44. The liquid stream continues through line 45 and flow-control valve 46 of the fourth and last flashing stage and discharges into separator 47. Vaporized carbon dioxide is vented from separator 47 by line 48 while the liquid, which is methanol with not more than about 2% of absorbed residual carbon dioxide on a molar basis, leaves through valved line 49 and is suitable for recycling to the top of contact column 19.

Pump 50 raises the pressure of the liquid methanol in line 49 sufficiently to cause its flow through line 51, heat exchanger 33 and line 20 to complete the recycling of the methanol to scrubbing column 19.

The vaporized carbon dioxide streams in lines 30 and 36 are combined in line 52 and the composite stream flows through heat exchanger 14 to help chill the land-fill gas entering exchanger 14 by way of line 13. The composite carbon dioxide stream discharges from exchanger 14 through line 53. The liquid mixture of water and methanol in line 17 is also passed through heat exchanger 14 to help chill the land-fill gas entering exchanger 14. The liquid mixture discharges from exchanger 14 through line 54, and preferably flows to a conventional plant which will separate the water and methanol so that the recovered methanol can be again injected through line 12 into the land-fill gas.

As an example illustrative of the invention, land-fill gas is supplied through line 10 at a pressure of 345 psia and a temperature of 40° F. and methanol is injected through line 12. The dehydrated gas resulting from cooling the gas in heat exchanger 14 to a temperature of −30° F. and elimination of condensed water and methanol in separator 16 discharges from line 18 at a pressure of 335 psia into column 19. Recycled methanol containing 1.4% of residual carbon dioxide on a molar basis enters column 19 through line 20 at a pressure of 330 psia and a temperature of −55° F. The scrubbed or product gas leaves column 19 through line 21 at a temperature of −50° F. and after passage through heat exchanger 14 has a temperature of 35° F. and a pressure of 325 psia.

The methanol with absorbed carbon dioxide leaves column 19 at a temperature of 0° F., is chilled to −6° F. by heat exchanger 24 and is further chillled to −27° F. by refrigerated exchanger 26. The pressure of the liquid in line 27 is dropped from 325 psia to 20 psia by reducing valve 28. The thus flashed stream has a temperature of −60° F.

The liquid in line 31 with control valve 32, in flowing through heat exchanger 33, is warmed to a temperature of −11° F. and discharges into separator 35 at a pressure of 17.5 psia to effect the second stage of carbon dioxide flashing. The liquid drained into line 37 with control valve 38 flows through line 39 and heat exchanger 24 where it is warmed to a temperature of −6° F. and thence discharged by line 40 into separator 41 of the third flashing stage at a pressure of 16.5 psia. Vaporized carbon dioxide is vented through valved line 42 while liquid leaves separator 41 through line 43 and flows through heat exchanger 44 where it is heated to a temperature of 10° F. The heated liquid discharges through line 45 and control valve 46 into separator 47 at atmospheric pressure for the last flashing stage. Vaporized carbon dioxide is vented through line 48 while liquid methanol is withdrawn through line 49 by pump 50 which raises the pressure of the methanol to 335 psia. The pumped methanol flows through line 51 and heat exchanger 33 where it is chilled to a temperature of −55° F. and thence is discharged by line 20 into the top of column 19 to complete the recycling of the methanol.

The flashed carbon dioxide in lines 30 and 36 are combined in line 52 and passed through heat exchanger 14 to give up refrigeration to the land-fill gas. The carbon dioxide in discharge line 53 is at a temperature of 35° F., has a purity of 90% by volume, and corresponds to 90% of the carbon dioxide entering the system with the land-fill gas. Methane is 8.2% by volume of the gas in line 53 and corresponds to 5.1% of the methane in the land-fill gas.

The condensed water and methanol drawn from separator 16 by valved line 17 at a temperature of −30° F. is also passed through heat exchanger 14 to help chill the land-fill gas and discharges into line 54 at a temperature of 35° F.

About 1.4% of the carbon dioxide in the land-fill gas issues through line 42 with a purity of 99.2% by volume, the remainder being hydrocarbons and a trace of vaporized methanol. Similarly, 5.6% of the carbon dioxide in the land-fill gas is discharged by line 48 with a purity of 97.7% by volume, the remainder being vaporized methanol and a trace of hydrocarbons.

The methane enrichment of the land-fill gas of the foregoing example can be seen in the following table which gives the composition by volume percentages of the dry gas entering column 19 and the product gas leaving column 19.

|  | Entering Gas | Leaving Gas |
|---|---|---|
| Methane | 56.3 | 85.5 |
| Other Hydrocarbons | 1.1 | 1.0 |
| Nitrogen | 6.5 | 10.2 |
| Oxygen | 0.4 | 0.6 |
| Hydrogen | 0.4 | 0.6 |
| Carbon Dioxide | 35.3 | 2.1 |

The product gas in line 21 contains 94.9% of the methane in the land-fill gas, the remainder of the methane having been lost with the carbon dioxide stream discharged by line 53 as already discussed.

In the example, the liquid methanol is recycled to the top of column 19 at the rate of about 6 mols for each mol of carbon dioxide entering the bottom of column 19 with the land-fill gas. Also, the stream passing through heat exchanger 26 is chilled indirectly by Freon refrigerant, while the heat of compression in the Freon may be utilized to warm the stream flowing through heat exchanger 44. Thus, the energy consumption of the system is minimized.

As previously mentioned, some methanol is lost as vapor with the carbon dioxide streams exiting in lines 42 and 48. Also, some methanol vapor is lost with the carbon dioxide discharged by line 53. However, the total loss of methanol at these three discharge lines is only 0.055% of the rate of liquid methanol recycled to contact column 19. Line 55 is used to inject enough methanol into the recycled methanol to compensate for the very small quantity of methanol lost as vapor through lines 42, 48 and 53.

The methanol injected through line 12 into mixing vessel 11 is preferably in amount sufficient to saturate the land-fill gas supplied by line 10. All of the methanol entering the system through line 12 leaves the system as liquid through line 54 even if the methanol injected through line 12 is somewhat in excess of that required to saturate the land-fill gas. In the example, 0.3 mol of methanol is supplied through line 12 for each 100 mols of land-fill gas entering mixing vessel 11 to saturate the gas. The liquid methanol discharged by line 54 contains all the moisture in the land-fill gas supplied to mixing vessel 11 and desirably is processed in any known manner to recover water-free methanol which can be recycled to line 12.

The embodiment of the invention described and shown diagrammatically in the accompanying drawing involves a single scrubbing column and multiple-stage flashing equipment in which the first stage is effected by substantially reducing the pressure of the methanol containing absorbed carbon dioxide and the next three stages achieve flashing or vaporization of carbon dioxide by warming the methanol. However, where the cost of power is low, it is possible to omit one flashing stage which depends on warming the methanol stream.

For example, if warming exchanger 44 is used to heat the methanol to a temperature of 20° F., there will be less than 1.4% on a molar basis of residual carbon dioxide in the methanol recycled by pump 50 and this will cause the methane-enriched gas leaving column 19 to have less than 2.1% by volume of carbon dioxide. However, the loss of vaporized methanol with the carbon dioxide vented by line 48 will be somewhat increased. At the same time, the warmer methanol passing through heat exchanger 33 will warm the stream in line 34 to a temperature higher than −11° F. Because of this higher temperature, the liquid in line 39 will now have substantially the same temperature of the liquid in line 40 of the previously described example. Hence, heat exchanger 24 and separator 41 are eliminated and the liquid in line 39 now flows directly to warming exchanger 44. The increased heat input at exchanger 44 to raise the temperature of the steam in line 45 to 20° F. must be compensated by increased refrigeration supplied by exchanger 26 particularly in the absence of heat exchanger 24.

In summary, the control variables of the process of this invention are such that:

1. The higher the pressure in the scrubbing column, the lower the carbon dioxide content of the scrubbed or product gas will be;
2. The lower the content of residual carbon dioxide in the methanol recycled to the scrubbing column, the lower the carbon dioxide content of the product gas will be; and
3. The lower the temperature of the methanol recycled to the column, the lower the carbon dioxide content of the product gas will be.

The energy consumption, i.e., refrigeration and heat, of the process diminishes as the pressure of the gas supplied to the scrubbing column increases and as the carbon dioxide content of that gas increases. For example, a land-fill gas containing 40% by volume of carbon dioxide supplied to the contact column at a pressure of 400 psia will consume less energy than would be required to process the same gas supplied at a pressure of 300 psia. Similarly, at any selected pressure in the scrubbing column, a land-fill gas containing 40% by volume of carbon dioxide will require a lower energy consumption than if it contained 30% by volume of carbon dioxide. In some cases, there may be no need for chilling exchanger 26 or warming exchanger 44 or both. A gas with a very high carbon dioxide content supplied at very high pressure to contact column 19 will cause the methanol to leave column 19 at such a high temperature that the stream of line 39 will be heated in exchanger 24 sufficiently to achieve the last stage of flashing of carbon dioxide from the methanol, i.e., to leave not more than about 2% on a molar basis of residual carbon dioxide in the methanol in separator 41; in such case, heating exchanger 44 and separator 47 are eliminated and the methanol in line 43 flows directly to pump 50.

Many variations and modifications of the invention will be apparent to those skilled in the art without departing from the spirit or scope of the invention. For example, single heat exchanger 14 can be replaced by two or three parallel heat exchangers to cool the land-fill gas of line 13 with the streams of lines 17, 21 and 52. Similarly, the land-fill gas in line 10 need not be dehydrated by the injection of methanol through line 12; in such case, mixing vessel 11, separator 16 and lines 17 and 54 would be eliminated. One known method of dehydrating the gas of line 10 is to pass the gas into contact with a desiccant; the dry gas would then flow through heat exchanger 14 directly into line 18 discharging into contact column 19. Also, the streams of lines 42 and 48 may be passed through heat exchanger 14 countercurrently to the land-fill gas of line 13 to help chill the land-fill gas. Accordingly, only such limitations should be imposed on the invention as are set forth in the appended claims.

What is claimed is:

1. A process for removing carbon dioxide from a gas containing at least about 50% by volume of methane and at least about 5% by volume of carbon dioxide, which comprises compressing said gas, dehydrating the compressed gas, chilling the dehydrated compressed gas by indirect heat exchange with countercurrent discharge streams of product gas and separated carbon dioxide, both said streams being hereinafter identified, scrubbing the chilled dehydrated compressed gas at a pressure in the range of about 200 to 600 psia with cold recycled methanol supplied at a temperature in the range of about −40° F. to −70° F., said recycled methanol containing not more than about 2% on a molar basis of absorbed carbon dioxide at the start of said scrubbing, passing the scrubbed gas containing not more than about 2.5% by volume of carbon dioxide as the aforesaid discharge stream of product gas, cooling the methanol withdrawn from said scrubbing and passing the cooled methanol through a pressure reducing valve to effect a substantial pressure drop and a first flashing separation of absorbed carbon dioxide from said methanol, heating said methanol after said first flashing separation by indirect heat exchange with the aforesaid recycled methanol to effect solely with said heating a second flashing separation of absorbed carbon dioxide from said methanol, passing carbon dioxide from said first and said second flashing separation as the aforesaid discharge stream of separated carbon dioxide, further heating said methanol after said second flashing separation to effect solely with said further heating at least one further flashing separation of absorbed carbon dioxide from said methanol, venting the further flashed carbon dioxide, and pumping said methanol after said further flashing separation as the aforesaid recycled methanol to effect the aforesaid indirect heat exchange and scrubbing.

2. The process of claim 1 wherein the cooling of the methanol withdrawn from the scrubbing comprises passing the methanol after the second flashing separation of absorbed carbon dioxide in indirect heat exchange with said withdrawn methanol.

3. The process of claim 1 wherein the cooling of the methanol withdrawn from the scrubbing comprises the use of external refrigeration in an amount that upon passage of the cooled methanol through the pressure reducing valve the resultant further cooled methanol after the first flashing separation will in the indirect heat exchange with the recycled methanol make the temperature of said recycled methanol drop below about −40° F.

4. The process of claim 1 wherein the compressed gas is dehydrated by injecting methanol to saturate said gas, chilling said saturated gas by indirect heat exchange with the countercurrent discharge streams of product gas and separated carbon dioxide thereby condensing all the moisture in said gas and said methanol, separating the condensate of moisture and methanol from the thus chilled and dehydrated gas, and passing said condensate in indirect heat exchange with said saturated gas.

5. The process of claim 1 wherein the further heating of the methanol comprises indirect heat exchange with the methanol withdrawn from the scrubbing and the use of external heat.

6. An apparatus for removing carbon dioxide from a pressurized gas containing methane as the principal component by scrubbing said gas with recycled methanol which comprises:
   a. a scrubbing column having a gas inlet in the bottom portion and a gas outlet in the top as well as a methanol inlet in the top portion and a methanol outlet in the bottom;
   b. a cooling exchanger connected to said methanol outlet and to a pressure reducing valve so that methanol withdrawn from said scrubbing column through said methanol outlet is cooled in flowing through said cooling exchanger to said reducing valve;
c. a first gas-liquid separator connected to the discharge end of said reducing valve;
d. a first warming heat exchanger connected to the liquid drain of said first separator and to a second gas-liquid separator so that liquid from said first separator is warmed in flowing through said first heat exchanger into said second separator;
e. a second warming heat exchanger connected to the liquid drain of said second separator and a third gas-liquid separator so that liquid from said second separator is further warmed in flowing through said second heat exchanger into said third separator;
f. a pump connected to receive liquid from said third separator and to recycle said liquid through said first heat exchanger in indirect exchange relation to the liquid passing through said first heat exchanger from said first separator; and
g. a pipe connected to conduct the recycle liquid from said first heat exchanger to said methanol inlet.

7. The apparatus of claim 6 wherein the coolant passage of the cooling exchanger is connected to receive the liquid from the second separator and to discharge said liquid into the third separator.

8. The apparatus of claim 7 wherein a third warming heat exchanger is connected to the liquid drain of the third separator and to a fourth gas-liquid separator so that liquid from said third separator is still further warmed in flowing through said third heat exchanger into said fourth separator, the liquid drain of said fourth separator being connected to the pump so as to recycle said liquid through the first warming heat exchanger.

9. The apparatus of claim 8 wherein a second cooling exchanger is connected to the cooling exchanger and to the pressure reducing valve so that liquid from said cooling exchanger is further cooled in flowing through said second cooling exchanger to said reducing valve.

* * * * *